(12) United States Patent
Mrugas

(10) Patent No.: US 11,007,049 B2
(45) Date of Patent: May 18, 2021

(54) SYNTHETIC LIGAMENT, METHOD OF PRODUCING SAME AND USE THEREOF

(71) Applicant: Robert Mrugas, Warsaw (PL)

(72) Inventor: Robert Mrugas, Warsaw (PL)

( * ) Notice: Subject to any disclaimer, the term of this patent is extended or adjusted under 35 U.S.C. 154(b) by 146 days.

(21) Appl. No.: 16/087,117

(22) PCT Filed: Mar. 23, 2017

(86) PCT No.: PCT/PL2017/000028
§ 371 (c)(1),
(2) Date: Sep. 21, 2018

(87) PCT Pub. No.: WO2017/164754
PCT Pub. Date: Sep. 28, 2017

(65) Prior Publication Data
US 2019/0099254 A1    Apr. 4, 2019

(30) Foreign Application Priority Data

Mar. 24, 2016   (PL) .......................... 416635

(51) Int. Cl.
*A61F 2/08* (2006.01)
*D04C 1/06* (2006.01)
(Continued)

(52) U.S. Cl.
CPC ................ *A61F 2/08* (2013.01); *A61L 27/16* (2013.01); *A61L 27/32* (2013.01); *C08L 23/06* (2013.01);
(Continued)

(58) Field of Classification Search
CPC ........ A61F 2/08; A61F 2/0805; A61F 2/0811; A61F 2002/0852; A61F 2/0063;
(Continued)

(56) References Cited

U.S. PATENT DOCUMENTS 3,176,316 A * 4/1965 Bodellbrucer ............ A61F 2/08
 623/13.19
3,613,120 A * 10/1971 McFarland, Jr. ......... A61F 2/08
 623/13.2
(Continued)

FOREIGN PATENT DOCUMENTS

| EP | 0145492 A2 | 6/1985 |
| EP | 0475889 A1 | 3/1992 |
| EP | 2275148 A1 | 1/2011 |

OTHER PUBLICATIONS

International Search Report of PCT/PL2017/000028 dated Jul. 11, 2017.

*Primary Examiner* — Alvin J Stewart
(74) *Attorney, Agent, or Firm* — McBee Moore & Vanik IP, LLC

(57) ABSTRACT

A synthetic ligament made of a plurality of polymer filaments comprising two intra-osseous portions (1), within which polymer filaments are oriented only longitudinally and are woven together longitudinally and knotlessly to form a dense weave, and one intra-articular portion (2), located between the two intra-osseous portions (1), which comprises loose filaments and is untwisted around its axis. A method of producing a synthetic ligament in which the step of weaving of the polymer filaments within the intra-osseous portions (1) is carried out by means of longitudinal and knotless weaving to obtain a dense weave, with polymer filaments within the intra-articular portion (2) of a ligament remaining loose. A use of a synthetic ligament as a medical implant for the reconstruction of ligaments and tendons, notably knee ligaments.

13 Claims, 3 Drawing Sheets

(51) Int. Cl.
  *A61L 27/16* (2006.01)
  *A61L 27/32* (2006.01)
  *C08L 23/06* (2006.01)

(52) U.S. Cl.
  CPC ........ *D04C 1/06* (2013.01); *A61F 2210/0057* (2013.01); *A61F 2230/0069* (2013.01); *A61F 2240/001* (2013.01); *A61F 2240/008* (2013.01); *A61L 2430/10* (2013.01); *D10B 2509/00* (2013.01)

(58) Field of Classification Search
  CPC ................ A61B 17/0401; A61B 17/04; A61B 2017/06185; A61B 17/06166; A61B 2017/06095; A61B 2017/061; A61B 17/1146
  See application file for complete search history.

(56) References Cited

U.S. PATENT DOCUMENTS

| | | | | |
|---|---|---|---|---|
| 3,971,670 | A * | 7/1976 | Homsy | A61F 2/08 156/196 |
| 4,127,902 | A * | 12/1978 | Homsy | A61F 2/08 623/13.11 |
| 4,149,277 | A * | 4/1979 | Bokros | A61F 2/08 623/13.2 |
| 4,187,558 | A * | 2/1980 | Dahlen | A61F 2/08 623/13.14 |
| 4,255,820 | A * | 3/1981 | Rothermel | A61F 2/08 623/13.11 |
| 4,301,551 | A * | 11/1981 | Dore | A61F 2/08 267/152 |
| 4,329,743 | A * | 5/1982 | Alexander | A61B 17/80 428/408 |
| 4,400,833 | A * | 8/1983 | Kurland | A61B 17/1146 623/1.32 |
| 4,455,690 | A * | 6/1984 | Homsy | A61F 2/08 623/13.15 |
| 4,781,191 | A * | 11/1988 | Thompson | A61B 17/30 606/151 |
| 4,917,699 | A | 4/1990 | Chervitz | |
| 4,917,700 | A * | 4/1990 | Aikins | A61F 2/08 623/13.19 |
| 5,004,474 | A * | 4/1991 | Frank | A61F 2/08 623/13.14 |
| 5,147,400 | A * | 9/1992 | Kaplan | A61F 2/06 623/13.18 |
| 5,197,983 | A * | 3/1993 | Berman | A61F 2/08 623/13.2 |
| 5,258,040 | A * | 11/1993 | Bruchman | A61F 2/08 57/201 |
| 5,263,984 | A * | 11/1993 | Li | A61F 2/08 623/13.18 |
| 5,376,118 | A * | 12/1994 | Kaplan | A61F 2/06 606/228 |
| 5,575,819 | A * | 11/1996 | Amis | A61F 2/08 623/13.13 |
| 8,172,901 | B2 * | 5/2012 | Altman | A61F 2/08 623/13.12 |
| 8,226,715 | B2 * | 7/2012 | Hwang | A61L 27/56 623/13.14 |
| 8,881,635 | B2 * | 11/2014 | Martin | D04B 1/22 87/6 |
| 9,060,854 | B2 * | 6/2015 | Altman | D04B 1/123 |
| 9,517,062 | B2 * | 12/2016 | Santangelo | A61B 17/0401 |
| 10,265,155 | B2 * | 4/2019 | Lu | A61P 29/00 |
| 10,329,698 | B2 * | 6/2019 | Clough | D04B 15/58 |
| 10,881,394 | B2 * | 1/2021 | Dumanian | A61B 17/06 |
| 2001/0044659 | A1 | 11/2001 | Laboureau | A61F 2/08 623/13.2 |
| 2004/0024457 | A1 * | 2/2004 | Boyce | A61F 2/08 623/13.17 |
| 2004/0267362 | A1 * | 12/2004 | Hwang | A61F 2/08 623/13.15 |
| 2005/0192581 | A1 * | 9/2005 | Molz | D04C 1/12 606/74 |
| 2007/0118217 | A1 * | 5/2007 | Brulez | A61F 2/08 623/13.2 |
| 2007/0270857 | A1 * | 11/2007 | Lombardo | A61B 17/0401 606/232 |
| 2008/0027542 | A1 * | 1/2008 | McQuillan | A61L 27/3662 623/13.11 |
| 2008/0300683 | A1 * | 12/2008 | Altman | D04B 1/123 623/13.11 |
| 2009/0018654 | A1 * | 1/2009 | Schmieding | A61B 17/1675 623/13.14 |
| 2009/0318962 | A1 * | 12/2009 | Spedden | A61L 17/005 606/228 |
| 2010/0298937 | A1 * | 11/2010 | Laurencin | A61L 27/14 623/13.14 |
| 2013/0226232 | A1 * | 8/2013 | Dumanian | A61B 17/06 606/224 |
| 2013/0345810 | A1 * | 12/2013 | Jaeger | A61F 2/0045 623/13.11 |
| 2014/0039620 | A1 * | 2/2014 | Cantournet | A61F 2/08 623/13.14 |
| 2014/0172096 | A1 * | 6/2014 | Koob | D04C 1/12 623/13.19 |
| 2017/0079769 | A1 * | 3/2017 | Greenhalgh | A61F 2/08 |
| 2017/0281327 | A1 * | 10/2017 | Kaplan | A61F 2/0811 |
| 2018/0000480 | A1 * | 1/2018 | Dumanian | A61B 17/0401 |
| 2018/0140415 | A1 * | 5/2018 | Engin | A61F 2/08 |
| 2018/0228596 | A1 * | 8/2018 | Wyland | A61B 17/0401 |

* cited by examiner

SYNTHETIC LIGAMENT, METHOD OF PRODUCING SAME AND USE THEREOF

CROSS REFERENCE TO RELATED APPLICATIONS

This application is a National Stage entry of International Application No. PCT/PL2017/000028 filed 23 Mar. 2017, which claims priority to Poland Patent Application No. P.416635, filed 24 Mar. 2016.

BACKGROUND

The invention relates to a synthetic ligament made of polymer fibres, a method of producing a synthetic ligament, and its use as a medical implant for the reconstruction of ligaments and tendons, notably knee ligaments.

DESCRIPTION OF RELATED ART

Over the last 20 years many attempts have been made to develop synthetic ligaments, whose major function would be to provide a support structure for the reconstruction of ligament tissue after trauma, to facilitate regeneration and resumption of ligament's natural function as well as to temporarily substitute for the traumatized tissue. Synthetic ligaments are designed so that their structure imitates as well as possible the structure of a natural ligament, providing for possibly best therapeutic effects following implantation.

Presently, a widely used method of ligament reconstruction with use of artificial implants is L.A.R.S. (Ligament Augmentation and Reconstruction System), which was developed and popularized throughout the world by French orthopaedist Jacques-Philippe Laboureau (Dijon, France). L.A.R.S. ligaments and their production methods are disclosed in patent descriptions EP 0 561 710 B1 and EP 1 006 947 B1. L.A.R.S. ligaments are made of polymer fibres of polyethylene terephthalate (PET), and their structure is very similar to the anatomical structure of natural ligaments: the structure of a L.A.R.S. ligament comprises two intra-osseous portions, which are nonmoving and which serve to secure the ligament within osseous channels, and one intra-articular section positioned between them, which is an active section enabling articular movement.

The characteristic feature of L.A.R.S. ligaments is the type of fibres used and their layout in the respective portions of the ligament. The intra-osseous portions comprise both longitudinal fibres and transverse fibres, which are woven together to form a mesh of a regular structure, whereas the intra-articular section comprises only longitudinal fibres, which remain loose. Additionally, the intra-articular section comprising loose fibres is twisted around its axis, depending on the intended placement of the implant, dextrorotarily or levorotarily. The characteristic method of producing such ligaments comprises an initial preparation of a mesh of longitudinal and transverse fibres, woven in the described way, and a next step of rolling it to obtain a cylinder. (see: FIG. 1 EP 1 006 947 B1 and FIG. 1 and FIG. 2 EP 0 561 710 B1).

The publication EP 0 145 492 A2 discloses a synthetic ligament having a similar anatomical, three-portion structure, which comprises a distinct intra-articular portion made of loose filaments longitudinally oriented and two intra-osseous portions made of a weave of longitudinal and transverse filaments.

An additional stage in the process of producing synthetic ligaments is a stage in which implants are given biocompatible properties. This is essential from the perspective of the therapeutic effect in that for an implant to be able to serve its function it must be neutral for the human body and must promote integration with the bone and growth of one's body cells (mainly fibroblasts, osteoblasts) into the artificial ligament structure to assure complete tissue regeneration.

The publication WO/2004/067051 discloses a method for the biomimetic functionalization of L.A.R. S. ligaments by peroxidation of implant's surface by means of ozonation followed by a step comprising radical polymerization of at least one monomer until a biologically active polymer is obtained covering the implant's surface, and as an optional step impregnating the implant with collagen and/or fibronectins. Other methods for providing and improving biocompatibility of artificial ligaments are also known, such as coating the surface of a polymer implant with specific biomimetic substances e.g. hydroxyapatite, whose purpose is to strengthen the bond between the polymer and the bone and to expedite the regeneration process.

From the point of view of therapeutic effects, not only the anatomical structure of an implant imitating the natural ligament structure is particularly important, but also its mechanical properties, such as strength and elasticity. Both these properties are crucially important for the ligament to maintain its functionality with passing time. To provide sufficient tear strength, the diameter of a synthetic ligament must be suitably large. As a result, implantation of a synthetic ligament within a knee joint involves the necessity of drilling an intra-osseous channel with a diameter corresponding to the ligament's diameter. A suitable elasticity of a synthetic ligament provides for its ability to reversibly deform in response to the forces acting on it, mimicking the functionality of a natural knee ligament.

While synthetic ligaments used presently emulate the anatomical structure of a natural ligament and are biocompatible, their mechanical properties such as tear strength and elasticity are still objects of study and optimization. Synthetic ligaments used presently, as compared to natural ligaments, are not stretchable or are stretchable insufficiently. Moreover, the diameter of presently used synthetic ligaments is relatively large in the context of the necessity to drill an intra-osseous channel. Elasticity of L.A.R.S. ligaments is poor (0-1%) while their strength amounting to 3600 N is achieved only in the case of a ligament with the diameter of 8-9 mm, constructed of 100 PET filaments.

A need therefore exists to develop a synthetic ligament characterized by an improved elasticity and whose tear strength would be improved or maintained with a simultaneous reduction of the ligament's diameter.

The Inventors were surprised to discover that a characteristic layout of filaments in a synthetic ligament and a unique type of weave of the filaments in the intra-osseous portions of the synthetic ligament influences the implant's mechanical properties. According to the invention it was possible to obtain a synthetic ligament characterised by an improved strength and better elasticity than previously used synthetic ligaments.

SUMMARY

The subject-matter of the invention is a synthetic ligament made of a plurality of polymer filaments comprising two intra-osseous portions, within which the filaments are woven together, and one intra-articular portion, located between the two intra-osseous portions, within which the polymer filaments constitute loose filaments, characterised in that the polymer filaments within the two intra-osseous portions are oriented only longitudinally and are woven together longitudinally and knotlessly to form a dense weave whereas the one intra-articular portion comprising loose filaments is untwisted around its axis.

The anatomical, three-part structure of the ligament according to the invention imitates the structure of a natural ligament. The intra-osseous portions are nonmoving and are housed within intra-osseous channels, their purpose being to provide material strength and stretch resistance. The intra-articular portion is an active part located within the joint, its purpose being to dissipate torque and shear strain as well as to enable fibroblast growth through the filaments.

The new feature of the ligamenat, namely, presence of only longitudinal filaments with complete absence of transverse filaments within the intra-osseous portions as well as a characteristic type of weaving of the longitudinal filaments within the intra-osseous portions determines the exceptional mechanical properties of the ligament according to the invention, i.e., its high strength and good elasticity. High strength makes it possible to produce a ligament whose diameter is about one third of the diameter of a standard ligament presently used on the market, at the same time maintaining high strength. Consequently, the diameter of an intra-osseous channel needed to secure the ligament according to the invention can be much smaller, which minimizes intervention in patient's healthy tissues and promotes the regeneration process. Good elasticity provides the ligament with the ability to elongate in response to forces applied and to return to its original shape, mimicking the natural ligament.

The Inventors have noticed that a particular weaving technique and a unique type of weave obtained thereby provided unexpected, exceptional mechanical properties of an implant according to the invention, i.e., considerably better strength of the implant over a long period of use and its better elasticity.

The Inventors have measured that the average strength of a ligament according to the invention was 3600 N with the ligament's diameter of 3 mm, while its elasticity was about 15%. The maximum strength of a ligament according to the invention during the tests performed by the Inventors was 4220 N, while its elasticity reached even 28%.

Additionally, the ligament exhibits a new feature of the intra-articular portion, namely, this portion is not twisted around its axis, either dextrorotarily or levorotarily, which allows for the same implant being universally usable in the right knee joint and the left knee joint.

DETAILED DESCRIPTION OF A PREFERRED EMBODIMENT

Preferably, the ligament according to the invention is formed as a tube of polymer filaments, which, upon applying a tensile force, assumes a shape of a two-layered tape. This constitutes an essential difference as compared to presently used ligaments, which are in the form of a cylinder made of a rolled mesh. The tape structure of the ligament according to the invention better imitates natural ligaments, allows for a conveyor-like motion during the articulation, thus reducing torque and shear forces present in the case of presently used ligaments.

Preferably, the ligament according to the invention comprises 16 to 124 polymer filaments and has a diameter between 2 and 7.1 mm. Most preferably, a ligament comprises 32 polymer filaments and has a diameter of 3 mm.

Preferably, polymer filaments in the ligament according to the invention are polyethylene filaments. Most preferably, polyethylene filaments are UHMWPE (ultra high molecular weight polyethylene) filaments.

Preferably, intra-osseous portions in a ligament according to the invention have a hydroxyapatite coating, which promotes integration with bone tissue, imparting to the ligament biocompatible properties.

Preferably, the ligament according to the invention additionally comprises at least one polymer cap (3) with a guiding strand (4) arranged at a terminal end of an intra-osseous portion (1). A cap with a guiding strand allows pulling a ligament through intra-osseous channels.

The subject-matter of the invention is also a method of producing a synthetic ligament made of a plurality of polymer filaments comprising two intra-osseous portions, within which the filaments are woven together, and one intra-articular portion, located between the two intra-osseous portions, within which the polymer filaments constitute loose filaments, which comprises the steps of preparation of polymer filaments, weaving of polymer filaments, and cleaning and sterilising a ligament, characterised in that the step of weaving of polymer filaments within the intra-osseous portions is carried out by means of longitudinal and knotless weaving until a dense weave is obtained, with polymer filaments within the intra-articular portion of a ligament remaining loose, until a tubular structure of a ligament is obtained, wherein the intra-articular portion comprising loose polymer filaments is left untwisted around its axis.

Preferably, the method according to the invention additionally comprises a step in which a pulling force is applied to a ligament having a tubular structure made of polymer filaments so that it is flattened to obtain a form of a two-layered tape.

Preferably, the method according to the invention additionally comprises a step in which both intra-osseous portions comprising woven polymer filaments are coated with hydroxyapatite.

Preferably, the method according to the invention additionally comprises a step in which guiding strands are arranged at terminal ends of intra-osseous portions.

Preferably, longitudinal and knotless weaving of polymer filaments within intra-osseous portions of a ligament in a method according to the invention is carried out in the following steps:
   a) preparing an even number of polymer filaments and arranging them around a circumference in an alternating layout of even-numbered and odd-numbered filaments,
   b) gathering spread polymer filaments in a single bundle, maintaining longitudinal orientation of filaments,
   c) moving even-numbered filaments one place counterclockwise, on the inside of the circumference, with odd-numbered filaments remaining on the outside of the circumference, maintaining longitudinal orientation of all filaments,
   d) moving odd-numbered filaments one place clockwise to replace neighbouring, but presently absent, even-numbered filaments, maintaining the longitudinal orientation of all filaments,
   e) moving even-numbered filaments one place counterclockwise, on the outside of the circumference, with odd-numbered filaments remaining on the inside of the circumference, maintaining longitudinal orientation of all filaments,
   f) moving odd-numbered filaments one place clockwise to replace neighbouring, but presently absent, even-numbered filaments, maintaining longitudinal orientation of all filaments, to define a starting position analogous as in step c), g) repeating cyclically steps c)-f) to obtain a desired length of knotless weave with longitudinal orientation of filaments for a first intra-osseous portion of a ligament, h) stopping the process of weaving and spinning a section of loose polymer filaments to obtain an intra-articular portion of a ligament, i) repeating cyclically steps c)-f) to obtain a desired length of knotless weave with longitudinal orientation of filaments for a second intra-osseous portion of a ligament.

Accordingly, the subject-matter of the invention is also a synthetic ligament produced by a method according to the invention.

The subject-matter of the invention is also a use of a synthetic ligament according to the invention as a medical implant for the reconstruction of ligaments and tendons, notably knee ligaments, including the anterior cruciate ligament (ACL), the posterior cruciate ligament (PCL), the medial collateral ligament (MCL), the lateral collateral ligament (LCL); as well as ligaments of shoulder joint, ligaments of ankle joint, and ligaments of hip joint.

The subject-matter of the invention is also a use of a synthetic ligament produced by a method according to the invention as a medical implant for the reconstruction of ligaments and tendons, notably knee ligaments, including the anterior cruciate ligament (ACL), the posterior cruciate ligament (PCL), the medial collateral ligament (MCL), the lateral collateral ligament (LCL); as well as ligaments of shoulder joint, ligaments of ankle joint, and ligaments of hip joint.

BRIEF DESCRIPTION OF DRAWINGS

The subject-matter of the invention has been presented in a drawing wherein.

The invention has been illustrated with example embodiments described below, which are not intended to limit the scope of invention.

EXAMPLE 1: A SYNTHETIC LIGAMENT ACCORDING TO THE INVENTION

Figure 1:
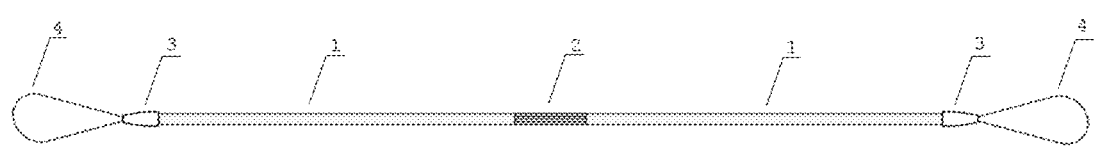
FIG. 1 presents a schematic structure of a synthetic ligament according to the invention.

The subject-matter of the invention has been presented in this example in a drawing wherein FIG. 1 presents a schematic anatomical structure of a ligament according to the invention.

A synthetic ligament is made of 32 UHMWPE filaments and comprises two intra-osseous portions (1), within which the polymer filaments are woven together, and one intra-articular portion (2), located between two intra-osseous portions (1), within which the polymer filaments constitute loose filaments. UHMWPE filaments within intra-osseous portions (1) are oriented only longitudinally and are woven together longitudinally and knotlessly to form a dense weave, whereas intra-articular portion (2) comprising loose polymer filaments is untwisted around its axis. Synthetic ligament is made in the form of a tubular structure of polymer filaments, which, upon applying a pulling force, assumes the form of a two-layered tape. The ligament's diameter is 3 mm. Terminal ends of intra-osseous portions (1) are equipped with polymer caps (3) with guiding strands (4).

EXAMPLE 2: A METHOD OF PRODUCING A SYNTHETIC LIGAMENT ACCORDING TO THE INVENTION

To produce a synthetic ligament employing a method according to the invention 32 UHMWPE filaments are prepared, which are then woven together by a longitudinal and knotless weaving technique. Weaving is carried out only in sections corresponding to intra-osseous portions (1) of a ligament, with filaments being left loose (unwoven) in a central section corresponding to intra-articular portion (2).

Figure 2:
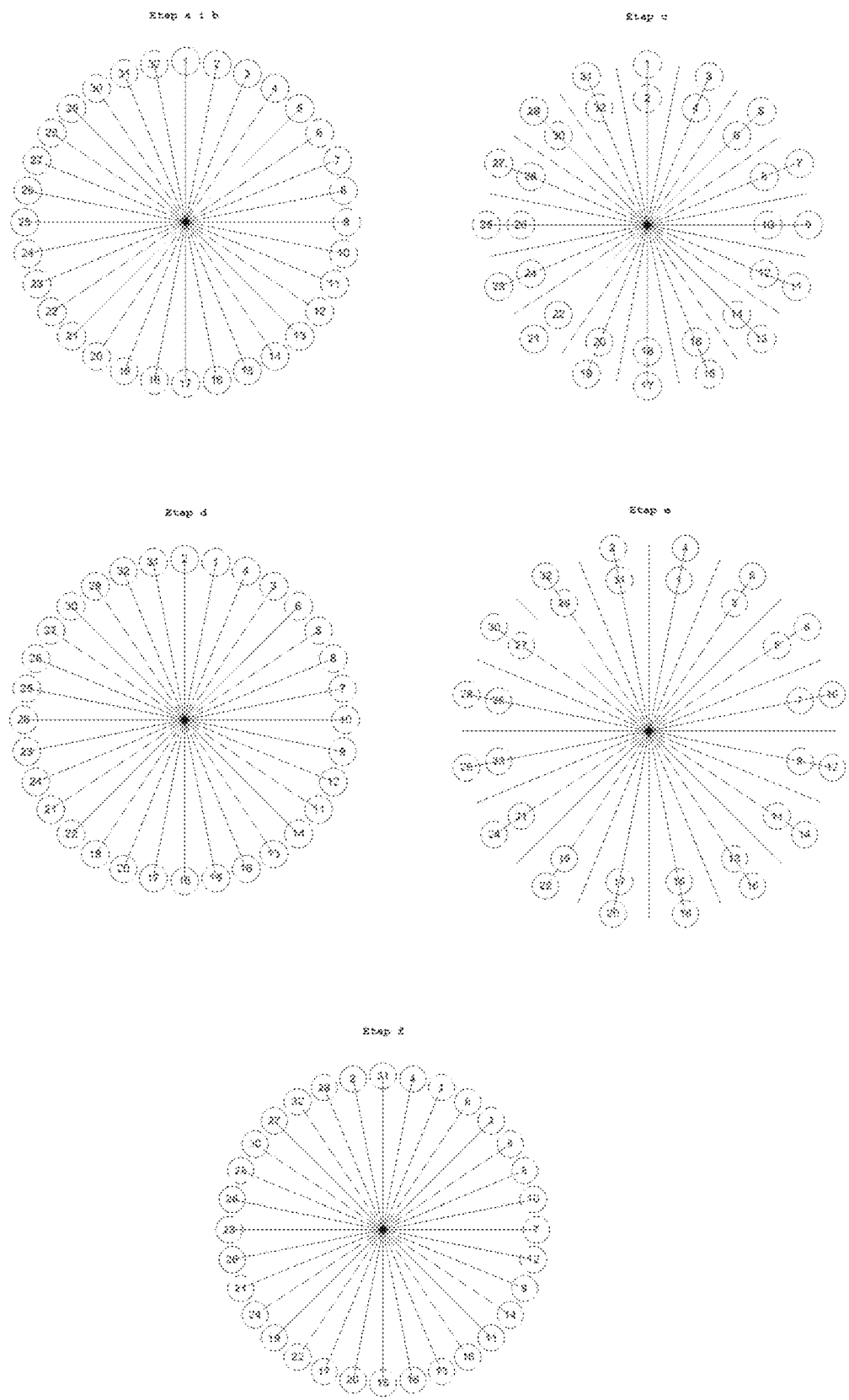
FIG. 2 presents steps of longitudinal and knotless weaving in a method of producing a ligament according to the invention.

Longitudinal and knotless weaving of 32 UHMWPE filaments within intra-osseous portions (1) of a ligament has been carried out in the following steps, with steps a)-f) being presented in FIG. 2:

a) an even number of UHMWPE filaments were prepared and arranged around a circumference in an alternating layout of even-numbered and odd-numbered filaments, b) spread polymer filaments were gathered in a single bundle, maintaining longitudinal orientation of filaments, c) even-numbered filaments were moved one place counterclockwise, on the inside of the circumference, with odd-numbered filaments remaining on the outside of the circumference, maintaining longitudinal orientation of all filaments, d) odd-numbered filaments were moved one place clockwise to replace neighbouring, but presently absent, even-numbered filaments, maintaining the longitudinal orientation of all filaments, e) even-numbered filaments were moved one place counterclockwise, on the outside of the circumference, with odd-numbered filaments remaining on the inside of the circumference, maintaining longitudinal orientation of all filaments, f) odd-numbered filaments were moved one place clockwise to replace neighbouring, but presently absent, even-numbered filaments, maintaining longitudinal orientation of all filaments, to define a starting position analogous as in step c), g) steps c)-f) were cyclically repeated until a desired length of knotless weave with longitudinal orientation of filaments was obtained for a first intra-osseous portion of ligament, h) the process of weaving was stopped and a section of loose polymer filaments was spun to obtain an intra-articular portion of ligament, i) steps c)-f) were cyclically repeated until a desired length of knotless weave with longitudinal orientation of filaments was obtained for a second intra-osseous portion of ligament.

As a result of carrying out the steps described above, a ligament was obtained in the form of a tube with the diameter of 3 mm. Intra-articular portion (2) comprising loose filaments was left untwisted around its axis. Next, a ligament in the form of a tube of polymer filaments was subject to a pulling force so that it was flattened until it assumed a form of a two-layered tape. At terminal ends of intra-osseous portions (1) polymer caps (3) were secured together with guiding strands (4). Additionally, both intra-osseous portions (1) of ligament comprising woven UHMWPE filaments were coated with hydroxyapatite. Next, a ligament was cleaned and sterilised and packed in a sterile container.

EXAMPLE 3: PRODUCING MODELS OF SYNTHETIC LIGAMENTS ACCORDING TO THE INVENTION HAVING VARIOUS NUMBERS OF FILAMENTS AND DIFFERENT DIAMETERS

Fourteen models of synthetic ligaments having various numbers of filaments and different diameters were produced according to the method described in Example 2. Numbers of filaments and diameters of respective models are shown in Table 1. On the basis of preliminary strength tests a theoretical tear strength was determined for respective models of ligaments, and results are shown in Table 1.

TABLE 1

| Model | Number of filaments | Ø of ligament [mm] | strength [N] |
|---|---|---|---|
| 1 | 22 | 2.8 | 2860 |
| 2 | 22 | 2.8 | 2860 |
| 3 | 24 | 3 | 3600 |
| 4 | 24 | 3 | 3600 |
| 5 | 24 | 3 | 3600 |
| 6 | 32 | 3.5 | 4160 |
| 7 | 32 | 3.5 | 4160 |
| 8 | 32 | 3.5 | 4160 |
| 9 | 40 | 4 | 5850 |
| 10 | 40 | 4 | 5850 |
| 11 | 40 | 4 | 5850 |
| 12 | 45 | 4.3 | 6000 |
| 13 | 45 | 4.3 | 6000 |
| 14 | 45 | 4.3 | 6000 |

EXAMPLE 4: STRENGTH TEST FOR A SYNTHETIC LIGAMENT ACCORDING TO THE INVENTION

A synthetic ligament obtained in Example 2 was tested in terms of its tear strength. The test was carried out in The Fabrics and Textile Articles Testing Laboratory of The Textile Institute in Łódź. The test was carried out employing a method compliant with the PN-EN ISO 13934-1:2013-07 standard: "Determination of maximum force and elongation at maximum force using the strip method".

The test was carried out for ligament samples with diameter of 3 mm made of 32 UHMWPE filaments, cleaned and sterile, which were obtained according to the method described in Example 2.

The test employed a Tinius Olsen H50KS testing machine, jaw type: flat with rubber padding and hydraulic/pneumatic pressure grip. Rate of extension was 100 mm/min, and distance between grips was 30 mm. Ligament strength test results are shown in Table 2.

TABLE 2

| Indicator | No. of sample | Value | Testing method |
|---|---|---|---|
| Maximum force for tested samples, [N] | 1 | 2968 | PN-EN ISO 13934-1:2013-07 |
|  | 2 | 4220 |  |
| Average maximum force, [N] |  | 3600 |  |

As it follows from Table 1, average maximum force for a synthetic ligament with 3 mm diameter made of 32 UHMWPE filaments was 3600 N. However, maximum force for a ligament according to the invention obtained in the test carried out by the Inventors was 4220 N.

This means that a 3 mm, 32-filament ligament according to the invention exhibits the same tear resistance as a 100-filament L.A.R.S. ligament with 9 mm diameter.

EXAMPLE 5: ELASTICITY TEST FOR A SYNTHETIC LIGAMENT ACCORDING TO THE INVENTION

A synthetic ligament obtained in Example 2 was tested in terms of its elasticity. The test was carried out in The Fabrics and Textile Articles Testing Laboratory of The Textile Institute in Łódź. The test was carried out employing a method compliant with the PN-EN ISO 2062:1997 standard: "Determination of breaking force and elongation at break of single strands".

The test was carried out for ligament samples with diameter of 3 mm made of 32 UHMWPE filaments, cleaned and sterile, which were obtained according to the method described in Example 2.

The test employed an Intron 3365, BM-B 205.00 testing machine. Rate of extension was 100 mm/min, and distance between grips was 30 mm.

Ligament elasticity test results are shown in Table 3.

TABLE 3

| No. of sample | Maximum force [cN] | Relative elongation at maximum force [%] |
|---|---|---|
| 1 | 169 657.9 | 7.69 |
| 2 | 108 381.1 | 5.50 |
| 3 | 239 656.8 | 18.13 |
| 4 | 223 157.6 | 13.07 |
| 5 | 168 033.5 | 28.38 |
| 6 | 294 475.6 | 11.59 |
| 7 | 322 395.9 | 19.52 |
| 8 | 342 149.8 | 21.35 |
| 9 | 272 286.6 | 9.11 |
| Avg. | 238 466.1 | 14.93 |
| Standard deviation | 78 087.22 | 7.44 |
| Coefficient of variation | 32.75 | 49.87 |
| Max. | 342 149.8 | 28.38 |
| Min. | 108 381.1 | 5.50 |

As it follows from Table 3, average relative elongation at average maximum force for a synthetic ligament with 3 mm diameter made of 32 UHMWPE filaments was 14.93%. However, the maximum observed value was 28.38%.

The above test has shown that a synthetic ligament according to the invention can be deformed up to 15% of its length during stretching and up to this value it retains the ability to return to its original state. Such high elasticity of a ligament according to the invention overcomes the deficiency of previously used ligaments, which are not stretchable.

EXAMPLE 6: BIOCOMPATIBILITY TEST FOR A SYNTHETIC LIGAMENT ACCORDING TO THE INVENTION

Figure 3:
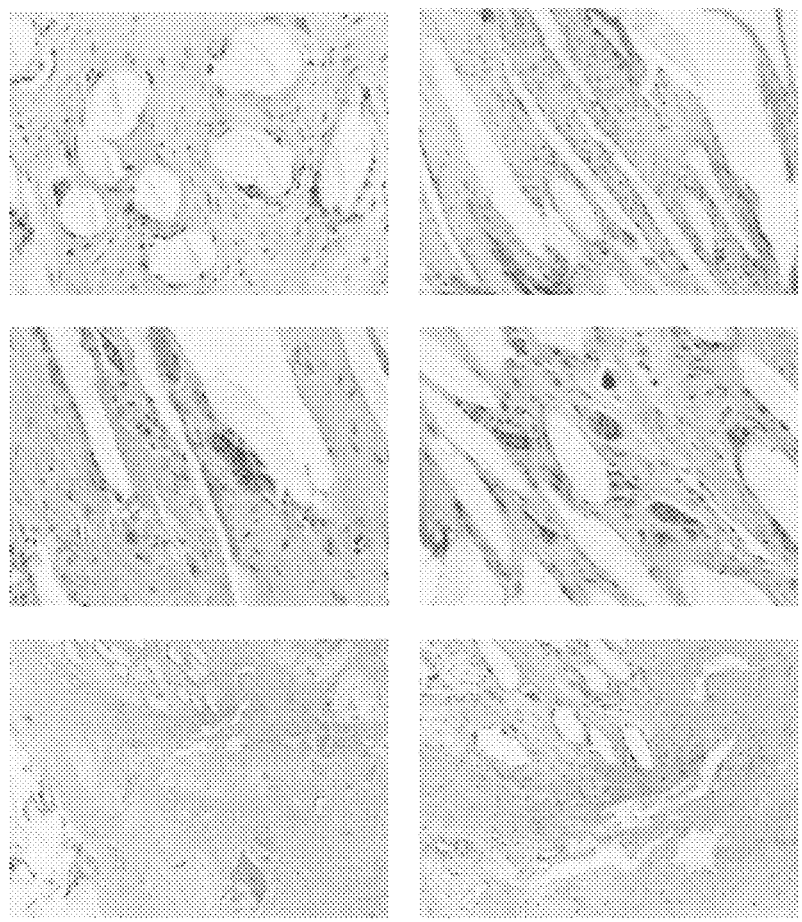
FIG. 3 presents microscopic images of a synthetic ligament with tissue ingrowth.

In order to test biocompatible properties of a synthetic ligament according to the invention, a reconstructive surgery was carried out to reconstruct a ruptured cruciate ligament in a knee joint of a dog. The surgery was performed in a Mastiff dog, aged 6 years, having a ruptured cruciate ligament. A synthetic ligament according to the invention, obtained as in Example 2, with diameter of 3 mm, made of 32 filaments, cleaned and sterile, was implanted into the dog's knee joint in order to replace a ruptured cruciate ligament. Two months after the surgery, tissues formed at the implantation site were observed under a microscope. Microscopic images of a ligament with tissue ingrowth are presented in FIG. 3.

The microscopic images show visible growth of mature granulation tissue around the present synthetic fibres, with mild exhibition of a granuloma reaction and presence of foreign-body giant cells. It was moreover observed that close to a terminal end of implantation the ground substance was more abundant in connective tissue stroma, there was less collagen fibres, and a focus of osseous metaplasia was also observable in that area. The microscopic image was not discrepant from what is observable around "standard" materials implanted in tissues.

The conducted study confirms that synthetic ligament is neutral for the body, that one's body cells grow into it enabling integration of the implant with the bone and assuring complete tissue regeneration.

The invention claimed is:

1. A synthetic ligament made of a plurality of polymer filaments comprising two intra-osseous portions, within which the polymer filaments are woven braided together, and one intra-articular portion, located between the two intra-osseous portions, within which the polymer filaments constitute loose filaments,
   wherein the synthetic ligament comprises 16 to 124 polymer filaments,
   wherein polymer filaments within the two intra-osseous portions are oriented only longitudinally and are braided together longitudinally and knotlessly to form a dense braid,
   whereas the one intra-articular portion comprising loose filaments is untwisted around its axis,
   wherein the polymer filaments consist of UHMWPE filaments, and
   wherein the synthetic ligament has a form of a braided tube having a hollow core and diameter between 2 and 7.1 mm that upon applying a tensile force assumes a form of a two-layered tape.

2. The synthetic ligament according to claim 1, wherein it comprises 32 polymer filaments and has a diameter of 3 mm.

3. The synthetic ligament according to claim 2, wherein an average maximum force of the synthetic ligament when tested with a method compliant with PN-EN ISO 13934-1: 2013-07 standard is 3600 N.

4. The synthetic ligament according to claim 1, wherein the intra-osseous portions have a hydroxyapatite coating.

5. The synthetic ligament according to claim 1, wherein it additionally comprises at least one polymer cap with a guiding strand arranged at a terminal end of the intra-osseous portion.

6. A product comprising a synthetic ligament according to claim 1 as a medical implant for the reconstruction of ligaments and tendons, optionally knee ligaments, including the anterior cruciate ligament (ACL), the posterior cruciate ligament (PCL), the medial collateral ligament (MCL), the lateral collateral ligament (LCL); optionally ligaments of shoulder joint, ligaments of ankle joint, and ligaments of hip joint.

7. The synthetic ligament of claim 1, wherein the synthetic ligament is made by a process comprising preparing polymer filaments, braiding the polymer filaments, and cleaning and sterilising a ligament, wherein the braiding of polymer filaments within the intra-osseous portions is carried out by means of longitudinal and knotless braiding until a dense braid is obtained, with polymer filaments within the intra-articular portion of a ligament remaining loose, until a tubular structure of a ligament is obtained.

8. The synthetic ligament of claim 7, wherein the synthetic ligament exhibits a tear strength greater than a tear strength of a ligament augmentation and reconstruction (L.A.R.S.) ligament of equal diameter and number of filaments when tested with a method compliant with PN-EN ISO 13934-1:2013-07 standard.

9. The synthetic ligament of claim 7, wherein longitudinal and knotless braiding of polymer filaments within the intra-osseous portions of a ligament is carried out in the following steps:
   a) preparing an even number of polymer filaments and arranging them around a circumference in an alternating layout of even-numbered and odd-numbered filaments,
   b) gathering spread polymer filaments in a single bundle, maintaining longitudinal orientation of filaments,
   c) moving even-numbered filaments one place counter-clockwise, on the inside of the circumference, with odd-numbered filaments remaining on the outside of the circumference, maintaining longitudinal orientation of all filaments, moving odd-numbered filaments one place clockwise to replace neighbouring, but presently absent, even-numbered filaments, maintaining the longitudinal orientation of all filaments,
   d) moving even-numbered filaments one place counter-clockwise, on the outside of the circumference, with odd-numbered filaments remaining on the inside of the circumference, maintaining longitudinal orientation of all filaments,
   e) moving odd-numbered filaments one place clockwise to replace neighbouring, but presently absent, even-numbered filaments, maintaining longitudinal orientation of all filaments, to define the starting position analogous as in step c),
   f) repeating cyclically steps c)-f) to obtain a desired length of knotless braid with longitudinal orientation of filaments for a first intra-osseous portion of a ligament,
   g) stopping the process of braiding, and spinning a section of loose polymer filaments to obtain an intra-articular portion of a ligament,
   h) repeating cyclically steps c)-f) to obtain a desired length of knotless braid with longitudinal orientation of filaments for a second intra-osseous portion of a ligament.

10. The synthetic ligament of claim 9, wherein the synthetic ligament comprises 32 polymer filaments and has a diameter of 3 mm.

11. The synthetic ligament according to claim 10, wherein an average maximum force of the synthetic ligament when tested with a method compliant with PN-EN ISO 13934-1: 2013-07 standard is 3600 N.

12. The synthetic ligament of claim 9, wherein the intra-osseous portions have a hydroxyapatite coating.

13. The synthetic ligament according to claim 9, wherein it additionally comprises at least one polymer cap with a guiding strand arranged at a terminal end of the intra-osseous portion.

* * * * *